United States Patent [19]

Sakata et al.

[11] Patent Number: 5,446,031

[45] Date of Patent: Aug. 29, 1995

[54] 1-β-D-ARABINOFURANOSYL-(E)-5-(2-HALOGENOVINYL) URACIL DERIVATIVES

[75] Inventors: Shinji Sakata; Haruhiko Machida; Katsushi Ijichi; Fumitaka Kano, all of Choshi, Japan

[73] Assignee: Yamasa Shuyu Kabushiki Kaisha, Chiba, Japan

[21] Appl. No.: 329,782

[22] Filed: Oct. 27, 1994

Related U.S. Application Data

[63] Continuation of Ser. No. 958,115, Dec. 23, 1992, abandoned.

[30] Foreign Application Priority Data

Apr. 24, 1991 [JP]  Japan .................. 3-94470

[51] Int. Cl.$^6$ .................. A61K 31/70; C07H 19/09
[52] U.S. Cl. .................. 514/50; 536/28.54
[58] Field of Search .................. 536/28.54; 514/50

[56] References Cited

U.S. PATENT DOCUMENTS

| | | | |
|---|---|---|---|
| 4,383,990 | 5/1983 | Coe et al. | 536/28.54 |
| 4,544,740 | 10/1985 | Szaboles nee Borbas et al. | 536/28.54 |

FOREIGN PATENT DOCUMENTS

| | | | |
|---|---|---|---|
| 0031128 | 7/1981 | European Pat. Off. | 536/28.54 |
| 0074101 | 3/1983 | European Pat. Off. | 536/28.54 |
| 0095294 | 11/1983 | European Pat. Off. | 536/28.54 |
| 0097376 | 1/1984 | European Pat. Off. | 514/47 |
| 0104857 | 4/1984 | European Pat. Off. | 536/28.54 |
| 259803 | 9/1988 | German Dem. Rep. | 536/28.54 |
| 56-87599 | 7/1981 | Japan | 536/28.54 |
| 163396 | 9/1984 | Japan | 536/28.54 |
| 145296 | 6/1988 | Japan | 536/28.54 |

OTHER PUBLICATIONS

Robins et al., "Conversion of Vinylsilanes to Vinyl Halides with Xenon Difluoride and Metal Halides. A Versatile New Route to 5-(2-Halovinyl)pyrimidein Nucleosides," *Tett. Lett.*, 31(39), 5633–5636 (1990).

Ashida et al., "Metabolism of 5'-Ether Prodrugs of 1-β-D-Arabinofuranosyl-E-5-(2-bromoviyl)uracil in Rats," *Biochem. Pharmacology*, 46(12), 2201–2207 (1993).

Kano et al., "5'-O-Alkyl and Acyl Prodrugs of 1-β-D-Arabinofuranosyl-E-5-(2-bromovinyl)uracil," *Antiviral Chem. & Chemotherapy*, 5(1), 74–82 (1993).

*Primary Examiner*—Douglas W. Robinson
*Assistant Examiner*—L. Eric Crane
*Attorney, Agent, or Firm*—Wenderoth, Lind & Ponack

[57] ABSTRACT

The present invention relates to a novel 1-β-D-arabinofuranosyl-(E)-5-(2-halogenovinyl)uracil derivative represented by the following formula (I), whose concentration in blood as XVAU can be kept high for many hours when it is administered orally.

The present invention also relates to an antiviral agent comprising as an active ingredient the compound of the present invention.

Further, the present invention relates to a method for treating viral diseases which comprises administering to a patient with a viral disease a safe and effective amount of the compound of the present invention.

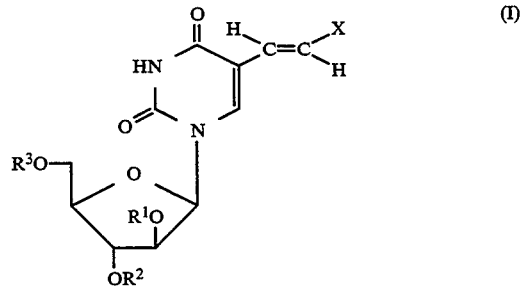

(I)

wherein X represents a halogen; and $R^1$, $R^2$, and $R^3$, which may be the same or different, each represent a hydrogen atom, a lower alkyl group or an aralkyl group, provided that $R^1$, $R^2$ and $R^3$ are not hydrogen at the same time.

3 Claims, No Drawings

1-β-D-ARABINOFURANOSYL-(E)-5-(2-HALOGENOVINYL) URACIL DERIVATIVES

This application is a continuation of now abandoned application, Ser. No. 07/958,115, filed Dec. 23, 1992, abandoned

TECHNICAL FIELD

The present invention relates to novel 1-β-D-arabinofuranosyl-(E)-5-(2-halogenovinyl)uracil derivatives having an antiviral activity.

BACKGROUND ART

It has been reported that 1-β-D-arabinofuranosyl-(E)-5-(2-halogenovinyl)uracil (XVAU) was synthesized first by Sakata and Machida and that a compound of this type possesses an extremely potent antiviral activity (see Japanese Patent Publication No. 48160/1982 and U.S. Pat. No. 4,386,076).

It is generally considered that one of the conditions required for a compound having an antiviral activity to be an excellent antiviral agent is that its concentration in blood can be kept high for many hours when it is administered orally.

Although it can be said that the above-described XVAU is a compound having a potent antiviral activity, the sustention of XVAU in blood when it is orally administered is still unsatisfactory when the above condition is taken into consideration.

An object of the present invention is therefore to provide novel XVAU derivatives which can increase the concentration of XVAU in blood and can keep it high for many hours when the derivatives are orally administered. If this object is attained, it would be expected that a treatment can be carried out efficiently with less amount of a medicine and/or fewer times of administration of the medicine.

DISCLOSURE OF THE INVENTION

We have made extensive studies in order to attain the above object, and, as a result, found that the desired object can be attained by the compounds having the following formula (I). The present invention has been accomplished on the basis of the above finding.

The present invention provides 1-β-D-arabinofuranosyl-(E)-5-(2-halogenovinyl)uracil derivatives (hereinafter referred to as the compounds of the present invention) having formula (I):

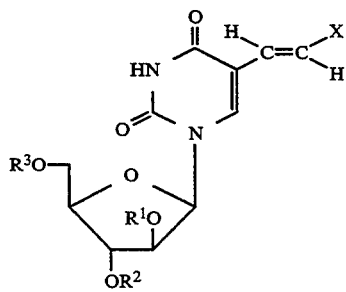

wherein X represents a halogen; and $R^1$, $R^2$ and $R^3$, which may be the same or different, represent a hydrogen atom, a lower alkyl group or an aralkyl group, provided that $R^1$, $R^2$ and $R^3$ are not hydrogen at the same time.

The present invention also provides an antiviral agent comprising as an active ingredient the above compound of the present invention.

The present invention further provides a method for the treatment of a viral disease, which comprises administering to a patient of the viral disease a safe and effective amount of the above compound of the present invention.

BEST MODE FOR CARRYING OUT THE INVENTION

Each of fluorine, iodine, bromine and chlorine can be exemplified as the halogen represented by X in the compounds of the present invention.

$R^1$, $R^2$ and $R^3$ may be the same or different from each other. However, those compounds in which $R^1$, $R^2$ and $R^3$ are hydrogen at the same time are already known, so that they do not fall within the scope of the present invention. Examples of the lower alkyl group represented by $R^1$, $R^2$ or $R^3$ include straight or branched chain alkyl groups having approximately 1 to 10 carbon atoms, such as methyl, ethyl, n-propyl, i-propyl, n-butyl, i-butyl, sec-butyl, tert-butyl, n-pentyl, i-pentyl, neo-pentyl, n-hexyl, i-hexyl, n-heptyl, n-octyl, n-nonyl and n-decyl. These alkyl groups may have one or more substituents such as hydroxyl, amino, carbonyl, or carboxyl group and a halogen at any position thereof.

The aralkyl group represented by $R^1$, $R^2$ or $R^3$ is an unsubstituted or substituted aralkyl group. There is no particular limitation on the type, the number and the position of a substituent contained in the substituted aralkyl group. Specific examples of the unsubstituted or substituted aralkyl group include benzyl, 1-phenylethyl, alkylbenzyl (methylbenzyl, ethylbenzyl, dimethylbenzyl, propylbenzyl, etc.), halobenzyl (fluorobenzyl, chlorobenzyl, bromobenzyl, dichlorobenzyl, chlorobromobenzyl, etc.), alkoxybenzyl (methoxybenzyl, ethoxybenzyl, dimethoxybenzyl, etc.), aminobenzyl (monoaminobenzyl, diaminobenzyl, etc.), hydroxybenzyl (monohydroxybenzyl, dihydroxybenzyl, etc.), nitrobenzyl, cyanobenzyl, phenethyl, picolyl and 3-indolylmethyl.

The compounds of the present invention may also be in the form of salts. For instance, metal salts such as a sodium salt, a potassium salt and a calcium salt can be exemplified.

Further, the chemical structure of the base moiety in the molecule of the compounds of the present invention may be either in ketonic form

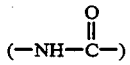

or in enolic form

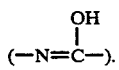

No particular limitation is imposed on the production of the compounds of the present invention.

In general, the desired compound of the present invention can be obtained by using as a starting compound a compound having formula (A):

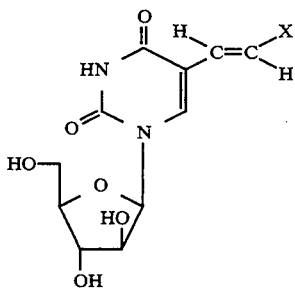

(wherein X represents a halogen), protecting with a suitable protecting group the hydroxyl groups of the compound other than those which are intended to be introduced with a lower alkyl group or an aralkyl group, introducing the lower alkyl group or the aralkyl group on the predetermined hydroxyl groups, and then removing the hydroxy protecting groups.

For instance, the compound of the present invention having a lower alkyl group or an aralkyl group at the 5'-position thereof can be produced in accordance with the following reaction scheme:

wherein $R^{3'}$ represents a lower alkyl group or an aralkyl group, X is as defined above, and Y and Z represent a hydroxy protecting group.

1. Preparation of Compound (B) from Compound (A):

The compound (A) is a known compound and can be prepared by a conventional method (see Japanese Patent Publications Nos. 48160/1982, 36836/1989 and 36837/1989, and U.S. Pat. No. 4,386,076).

Any protecting group can be introduced on the hydroxyl group at the 5'-position of the compound (A) as long as it can selectively protect the 5'-position. Specific examples of the protecting group include tri-lower alkylsilyl groups such as trimethylsilyl, triisopropylsilyl, tert-butyldimethylsilyl, tert-butyldiphenylsilyl, methyl-di-tert-butylsilyl and thexyldimethylsilyl.

The protecting group can be introduced by a conventional method. For instance, the compound (B) can be prepared by using 1- to 1.5-fold moles of a silylating agent (e.g., tri-lower alkylsilyl halide) for 1 mole of the compound (A), and reacting them in a reaction solvent (e.g., a solvent such as pyridine, picoline, diethylaniline, dimethylaminopyridine, dimethylformamide, acetonitrile, tetrabutyl amine or triethyl amine, or a mixture thereof) at a temperature of 0° to 50° C. for 1 to 30 hours.

2. Preparation of Compound (C) from Compound (B):

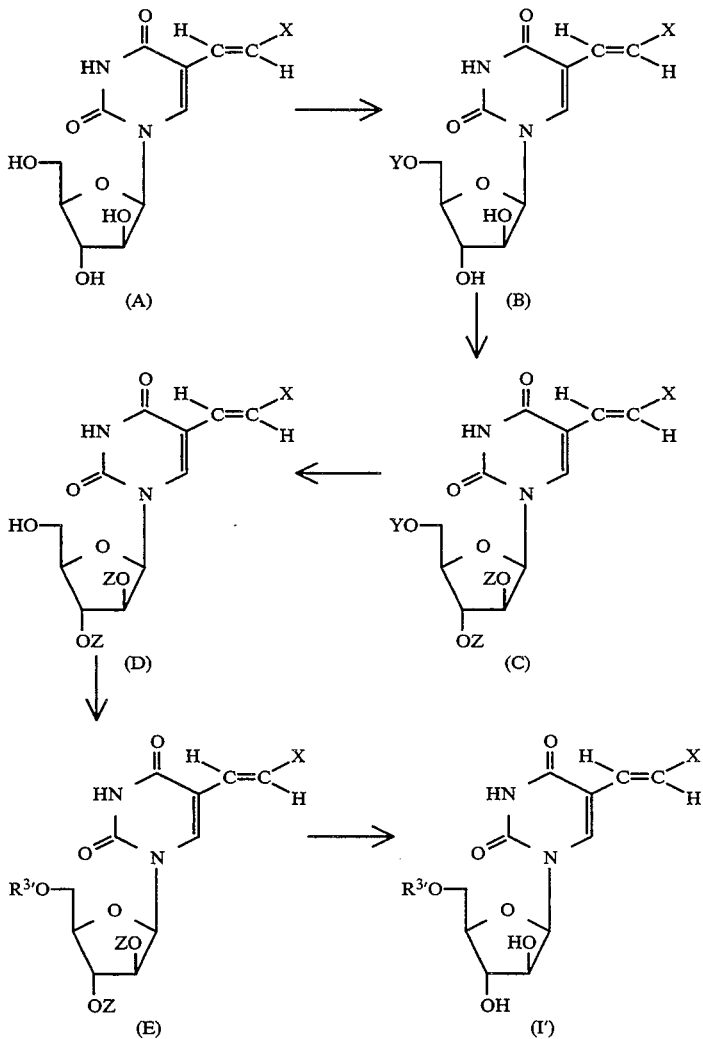

There is no particular limitation on the protecting group to be introduced on the hydroxyl groups at the 2'-and 3'-positions of the compound (B). There should however be used such a protecting group that is removed under the conditions which are different from those for the removal of the protecting group introduced on the hydroxyl group at the 5'-position. For example, in the case where a silyl group is used as the hydroxy protecting group at the 5'-position, it is recommended that a cyclic ether-type protecting group represented by the following formula (F) be used as the protecting group to be introduced on the hydroxyl groups at the 2'- and 3'-positions:

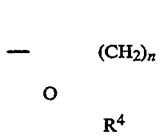

(F)

wherein $R^4$ represents a hydrogen atom, an alkyl group or an alkoxyl group, and n represents the integer 3 or 4.

Specifically, 2-tetrahydrofuryl, 2-tetrahydropyranyl, 4-methoxy-2-tetrahydropyranyl and the like can be exemplified.

The compound (C) can be prepared by introducing, by a conventional method, the above cyclic ether-type protecting group on the hydroxyl groups at the 2'- and 3'-positions of the compound (B). Explanation will be given by taking 2-tetrahydropyranyl as a specific example: the compound (C) can be prepared by using 2- to 6-fold moles of 3,4-dihydro-2H-pyrane for 1 mole of the compound (B), and reacting them without using any reaction solvent or in a proper reaction solvent (a solvent such as dioxane, tetrahydrofuran, ethyl ether, benzene, ethyl acetate, dichloromethane or dimethylformamide, or a solvent mixture thereof), in the presence of an acid catalyst (hydrochloric acid, p-toluenesulfonic acid, an ion-exchange resin (H type) or the like) at a temperature of 0° to 50° C.

3. Preparation of Compound (D) from Compound (C):

The compound (D) can be prepared by removing the hydroxy protecting group at the 5'-position of the compound (C).

The hydroxy protecting group at the 5'-position can be removed by any method as long as it is a method usually adopted for the removal of the protecting group used. It is however necessary to carry out the above deprotection by such a method and under such conditions that only the hydroxy protecting group at the 5'-position can be removed without simultaneously causing the removal of the hydroxy protecting groups at the 2'- and 3'-positions.

For instance, in the case where a tri-lower alkylsilyl group is used as the hydroxy protecting group at the 5'-position, a treatment with ammonium fluoride, alkaline hydrolysis or the like may be adopted.

4. Preparation of Compound (E) from Compound (D):

The compound (E) can be prepared by introducing a desired substituent represented by $R^{3'}$ to the 5'-position of the compound (D).

Specifically, this preparation can be carried out by using, for 1 mole of the compound (D), 1- to 3-fold moles of a reaction derivative represented by the formula:

$$HalR^{3'} \tag{G}$$

wherein Hal is a halogen, and $R^{3'}$ is as defined above; and reacting them in a reaction solvent (a solvent such as pyridine, dioxane, tetrahydrofuran, acetonitrile, dimethylformamide or ethyl ether, or a mixture thereof) at a temperature of 0° to 100° C. The above reaction can be carried out efficiently by adding a suitable amount of sodium hydride to the reaction solution.

5. Preparation of Compound (I') from Compound (E):

The compound of the present invention represented by formula (I') can be prepared by removing the hydroxy protecting groups at the 2'- and 3'-positions of the compound (E).

The hydroxy protecting groups can be removed by any method as long as it is a method usually adopted for the removal of the protecting group used. For instance, in the case where a cyclic ether-type protecting group is used, acidic hydrolysis with the use of an acid catalyst may be adopted.

Further, the compound of the present invention having at the 3'-position thereof a lower alkyl group or an aralkyl group can be produced, for example, in accordance with the following reaction scheme:

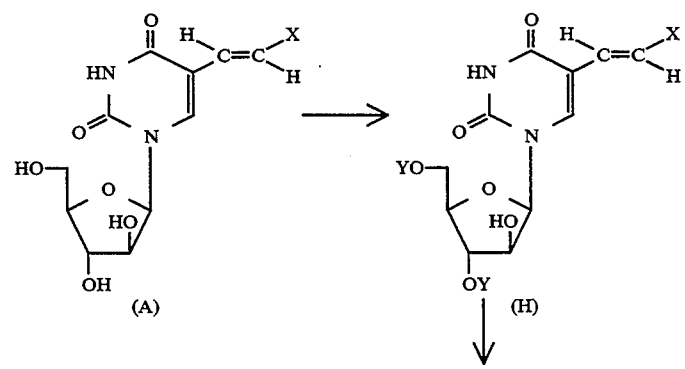

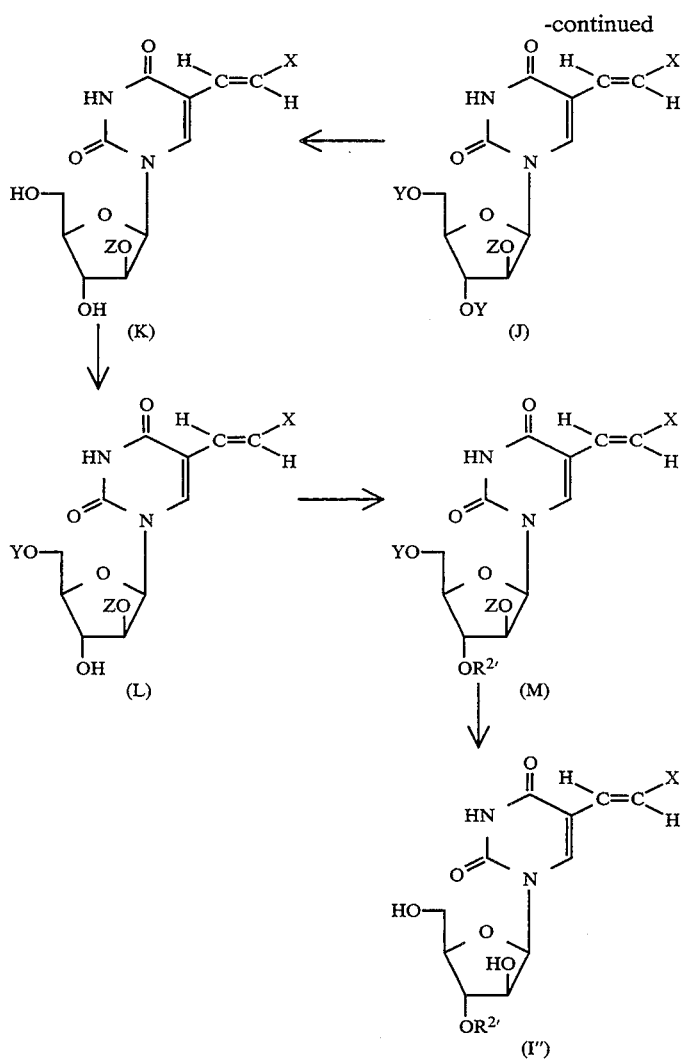

wherein R²' represents a lower alkyl group or an aralkyl group, and X, Y and Z are as defined above.

1. Preparation of Compound (H) from Compound (A):

No particular limitation is imposed on the hydroxy protecting group to be introduced to the 5'- and 3'-positions of the compound (A). It is however preferable to use a protecting group which can protect the hydroxyl groups at the 5'- and 3'-positions at the same time. Examples of such protecting groups include tetraalkyldisiloxanyl groups such as tetraisopropyldisiloxanyl and tetramethyldisiloxanyl.

The introduction of the protecting group can be carried out by a conventional method, and may be accomplished by a method similar to the method of introducing a tri-lower alkylsilyl group described in the aforedescribed "Preparation of Compound (B) from Compound (A)" section.

2. Preparation of Compound (J) from Compound (H):

No particular limitation is also imposed on the protecting group to be introduced on the hydroxyl group at the 2'-position of the compound (H). However, a protecting group that is removed under the conditions which are different from those for the removal of the protecting group introduced on the hydroxyl groups at the 5'- and 3'-positions is used. A cyclic ether-type protecting group represented by formula (F) exemplified in the aforedescribed "Preparation of Compound (C) from Compound (B)" section can be used as such protecting group, and the protecting group can be introduced on the hydroxyl group at the 2'-position by the same method as is described previously.

3. Preparation of Compound (K) from Compound (J):

The removal of the hydroxy protecting groups at the 3'- and 5'-positions are carried out by such a method and under such conditions that only these protecting groups can be removed without simultaneously removing the hydroxy protecting group at the 2'-position.

In the case where a tetraalkyldisiloxanyl group is used as the hydroxy protecting group at the 3'- and 5'-positions, a treatment with ammonium fluoride, alkaline hydrolysis or the like can be adopted.

4. Preparation of Compound (L) from Compound (K):

A tri-lower alkylsilyl group can be used as the hydroxy protecting group at the 5'-position, and it can be introduced to the 5'-position by the same method as is described previously.

5. Preparation of Compound (M) from Compound (L):

The compound (M) can be prepared by introducing a desired substituent represented by R²' to the 3'-position of the compound (L).

Specifically, the compound (M) can be obtained by using a reactive derivative represented by the formula:

$$HalR^{2'} \qquad (N)$$

wherein Hal and $R^{2'}$ are as defined above; and carrying out a reaction in the same manner as in the aforedescribed "Preparation of Compound (E) from Compound (D)" section.

6. Preparation of Compound (I″) from Compound (M):

The compound of the present invention represented by formula (I″) can be prepared by removing the hydroxy protecting groups at the 5′- and 2′-positions of the compound (M).

The protecting groups can be removed under the same conditions as in the aforedescribed "Preparation of Compound (I′) from Compound (E)" section.

Furthermore, the compound of the present invention having a lower alkyl group and/or an aralkyl group at the 3′- and 5′-positions can be produced, for instance, in accordance with the following reaction scheme:

from Compound (E)" or "Preparation of Compound (I″) from Compound (M)" section.

It is a matter of course that the compounds of the present invention which are not specifically described in the above description can also be prepared appropriately with reference to the above reaction schemes.

The compounds of the present invention thus obtained can be isolated and purified by any conventional means used for isolation and purification of nucleosides such as chromatography, recrystallization or the like.

In the case where an intermediate is needed to be isolated and purified in the course of the above-described production processes, it can also be isolated and purified by the above means.

The compounds of the present invention can be orally or parenterally administered to animals including a human by various administration routes. As will be

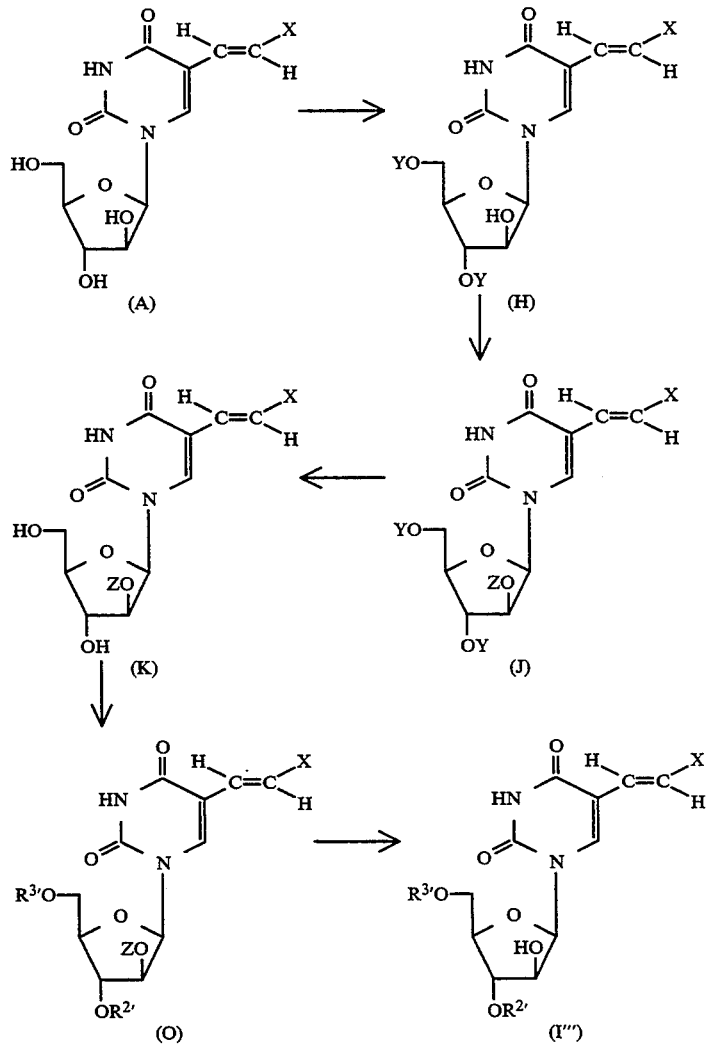

wherein X, Y, Z, $R^{2'}$ and $R^{3'}$ are as defined above.

In the above reaction scheme, the preparation of the compound (O) from the Compound (K) can be carried out in the same manner as in the aforedescribed "Preparation of Compound (E) from Compound (D)" or "Preparation of Compound (M) from Compound (L)" section. The preparation of the compound (I‴) from the compound (O) can be accomplished in the same manner as in the aforedescribed "Preparation of Compound (I′)

clear from the data obtained in Test Example which will be described later, oral administration is particularly preferred.

The compounds of the present invention can be made into solid form preparations such as powders, granules, capsules and tablets, and liquid form preparations such as syrups and elixirs, which are suitable for oral administration. These preparations can be prepared by a conventional method, i.e., by adding pharmaceutically acceptable additives to the compounds of the present invention. Moreover, they can also be formed into sustained release preparations in accordance with a known technique.

To prepare solid form preparations for oral administration, the compound of the present invention is mixed with an excipient such as lactose, starch, crystalline cellulose, calcium lactate, calcium monohydrogenphosphate, magnesium aluminometasilicate or silicic anhydride to obtain a powder; or a binding agent such as refined sugar, hydroxypropyl cellulose or polyvinylpyrrolidone, and a disintegrating agent such as carboxymethyl cellulose or carboxymethyl cellulose calcium are added to the above-obtained powder, and the resulting mixture is subjected to wet or dry granulation to obtain a granule. A tablet can be prepared by compressing the above-obtained powder or granule, or a mixture of the powder or granule and a lubricant such as magnesium stearate or talc. An enteric-coated preparation can be prepared by coating the above granule or tablet with an enteric base such as hydroxypropylmethylcellulose phthalate or a methyl methacrylate copolymer. A sustained release preparation can be prepared by coating the above granule or tablet with ethyl cellulose, carnauba wax or a hydrogenated oil. To prepare a capsulated preparation, the above powder or granule is charged into a hard capsule; or the compound of the present invention is first dissolved in glycerin, polyethylene glycol, sesame oil or olive oil and then coated with a gelatin film to obtain a soft capsule.

To prepare liquid preparations for oral administration, the compound of the present invention and a sweetener such as refined sugar, sorbitol or glycerol are dissolved in water to obtain a clear syrup; and essential oil or ethanol is further added to the above-obtained syrup to obtain an elixir; or gum arabic, tragacanth gum, polysorbate 80 or sodium carboxymethyl cellulose is further added to the above syrup to obtain an emulsion or suspension. These liquid preparations may also contain flavoring agents, colorants, preservatives and the like, if desired.

The dosage of the compound of the present invention depends on the age, the body weight and the condition of a patient. However, in general, approximately 3 to 300 mg, preferably 15 to 150 mg, is administered per day per individual, desirably at one time or several times (about 2 or 3 times).

EXAMPLES

The present invention will now be described more specifically by referring to the following Reference Examples, Examples (synthesis examples), Test Example and Preparation Examples.

Reference Example 1

1-(2,3-Di-O-tetrahydropyranyl-$\beta$-D-arabinofuranosyl)-(E)-5-(2-bromovinyl)uracil (Starting Compound 1)

6.98 g (20 mmol) of 1-$\beta$-D-arabinofuranosyl-(E)-5-(2-bromovinyl)uracil (BVAU) was dissolved in dimethylformamide (30 ml). To this solution were added 4.49 g (44 mmol) of imidazole and 3.32 g (22 mmol) of t-butyldimethylsilyl chloride, and the mixture was stirred at room temperature for 90 minutes. The solvent was removed by distillation under reduced pressure, and the residue was partitioned between ethyl acetate and saturated aqueous ammonium chloride. The organic layer was then washed with a saturated saline solution and dried over anhydrous sodium sulfate. The solvent was removed by distillation, and the residue (the compound having t-butyldimethylsilyl at the 5'-O-position) was dissolved in dichloromethane (70 ml). To this solution were added dihydropyrane (8 ml) and p-toluenesulfonic acid monohydrate (1.11 g), and the mixture was stirred at room temperature for 2 hours. A saturated sodium hydrogencarbonate solution (50 ml) was added to the reaction mixture to terminate the reaction. Thereafter, the organic layer was washed with a saturated saline solution and dried over anhydrous sodium sulfate. The solvent was removed by distillation, and the residue (the compound having t-butyldimethylsilyl at the 5'-O-position and tetrahydropyranyls at the 2'-O- and 3'-O-positions) was dissolved in tetrahydrofuran (100 ml). To this solution was added tetrabutylammonium fluoride (1M tetrahydrofuran solution, 25 ml), and the mixture was stirred at room temperature for 1 hour. The reaction mixture was concentrated in vacuo, and the residue was partitioned between ethyl acetate and water. The organic layer was washed with a saturated saline solution and dried over anhydrous sodium sulfate. The solvent was removed by distillation, and the residue was purified by silica gel column chromatography (silica gel 400 g, eluent: hexane/ethyl acetate $\frac{2}{3}$) to obtain 8.82 g (yield: 85% from BVAU) of the title compound as a foamy substance.

Elementary analysis: for $C_{21}H_{29}N_2O_8Br$ Calculated: C, 48.75; H, 5.65; N, 5.41 Found: C, 49.05; H, 5.78; N, 5.07

Reference Example 2

1-(2,3-Di-O-tetrahydropyranyl-$\beta$-D-arabinofuranosyl)-(E)-5-(2-chlorovinyl)uracil (Starting Compound 2)

By using 6.09 g (20 mmol) of 1-$\beta$-D-arabinofuranosyl-(E)-5-(2-chlorovinyl)uracil (CVAU), 7.85 g (yield: 83% from CVAU) of the title compound was obtained in the same manner as in Reference Example 1.

Elementary analysis: for $C_{21}H_{29}N_2O_8Cl$ Calculated: C, 53.33; H, 6.18; N, 5.92 Found: C, 53.44; H, 6.19; N, 5.75

Reference Example 3

1-(2,3-Di-O-tetrahydropyranyl-$\beta$-D-arabinofuranosyl)-(E)-5-(2-iodovinyl)uracil (Starting Compound 3)

By using 1.38 g (3.48 mmol) of 1$\beta$-D-arabinofuranosyl-(E)-5-(2-iodovinyl)uracil (IVAU), 1.15 g (yield: 59% from IVAU) of the title compound was obtained in the same manner as in Reference Example 1.

Elementary analysis: for $C_{21}H_{29}N_2O_8I$ Calculated: C, 44.69; H, 5.18; N, 4.96 Found: C, 44.74; H, 5.32; N, 5.02

Reference Example 4

1-(5-O-t-butyldimethylsilyl-2-O-tetrahydropyranyl-$\beta$-D-arabinofuranosyl)-(E)-5-(2-bromovinyl)uracil (Starting Compound 4)

To a solution of 3.49 g (10 mmol) of BVAU in pyridine (50 ml) was added 4.49 ml (13.6 mmol) of tetraisopropyldisiloxane-1,3-dichloride under ice-cooling, and the mixture was stirred for 2 hours. The reaction solution was concentrated to dryness. To the residue was added 100 ml of water, and the mixture was extracted with ethyl acetate. The organic phase was washed with water and dried over anhydrous sodium sulfate. The solvent was then removed by distillation, and the residue was chromatographed in a silica gel (70 g) column to isolate the product. The powder thus obtained was washed with water, and dried to obtain 5.24 g (88.6%) of a silylated compound.

4.8 g (8 mmol) of the silylated compound was dissolved in dichloromethane (70 ml). To this solution were added 424 mg (0.3 equivalent) of p-toluenesulfonic acid and 2.16 ml (3 equivalents) of 3,4-dihydro-2H-pyrane, and the mixture was stirred at room temperature for 3 hours. 1 ml of pyridine was added to the reaction solution, and the solvent was removed by distillation. 150 ml of tetrahydrofuran was added to the residue, and the residue was dissolved therein. To this mixture was added 9.6 ml of tetrabutylammonium fluoride, and the mixture was stirred for 30 minutes. The reaction mixture was concentrated to dryness. The residue was partitioned between water and ethyl acetate and then chromatographed in a silica gel (200 g) column to obtain a compound having tetrahydropyranyl at the 2'-O-position.

2.83 g (6.68 mmol) of the compound thus obtained was dissolved in dimethylformamide. To this solution were added 1.50 g (2.2 equivalents) of imidazole and 1.66 g (1.1 equivalents) of t-butyldimethylchlorosilane at room temperature, and the mixture was stirred at room temperature for 1 hour. The reaction mixture was concentrated to dryness. The residue was dissolved in ethyl acetate, washed with aqueous ammonium chloride, then washed with a saturated saline solution, and dried over anhydrous sodium sulfate. The organic layer was concentrated to dryness and then-chromatographed in a silica gel column to obtain 2.26 g (yield: 63%) of the title compound as a foamy substance.

Elementary analysis: for $C_{22}H_{36}N_2O_7BrSi$ Calculated: C, 48.17; H, 6.62; N, 5.11 Found: C, 48.33; H, 6.53; N, 5.09

Example 1

1-(5-O-benzyl-$\beta$-D-arabinofuranosyl)-(E)-5-(2-bromovinyl)uracil (Compound 1)

The starting compound 1 (517 mg, 1.0 mmol) was dissolved in tetrahydrofuran (5 ml ). To this solution was added 60% oily sodium hydride (72 mg, 3.0 mmol), and the mixture was stirred at room temperature for 10 minutes. Subsequently, benzyl bromide (188 mg, 1.1 mmol) was added to the mixture, and the reaction was carried out at room temperature for 19 hours. The reaction solution was diluted with ethyl acetate (30 ml). The diluted solution was washed with saturated ammonium chloride (20 ml) and a saturated saline solution (10 ml) and dried over anhydrous sodium sulfate. The solvent was removed by distillation, and the residue was dissolved in methanol (10 ml). To this solution was added p-toluenesulfonic acid monohydrate (76 mg, 0.4 mmol). The mixture was stirred at room temperature for 5 hours and then cooled overnight. The crystalline precipitate was collected by filtration and dried to obtain 220 mg (yield: 50%) of the title compound. A portion of the compound was recrystallized from ethanol to provide a sample for instrumental analysis.

Melting point: 203°–204° C. (decomposed)

Elementary analysis: for $C_{18}H_{19}N_2O_6Br$ Calculated: C, 49.22; H, 4.36; N, 6.38 Found: C, 49.04; H, 4.23; N, 6.52

Example 2

1-{5-O-(4-chlorobenzyl)-$\beta$-D-arabinofuranosyl}-(E)-5-(2-bromovinyl)uracil (Compound 2)

From the starting compound 1 (1.03 g, 2.0 mmol), 650 mg (yield: 69%) of the title compound was obtained in the same manner as in Example 1, using p-chlorobenzyl bromide (452 mg, 2.2 mmol). A portion of the compound obtained was recrystallized from ethanol-ethyl acetate (1:1) to provide a sample for instrumental analysis.

Melting point: 211°–212° C. (decomposed)

Elementary analysis: for $C_{18}H_{18}N_2O_6BrCl$ Calculated: C, 45.64; H, 3.83; N, 5.91 Found: C, 45.75; H, 3.87; N, 6.02

Example 3

1-{5-O-(4-bromobenzyl)-$\beta$-D-arabinofuranosyl}-(E)-5-(2-bromovinyl)uracil (Compound 3)

From the starting compound 1 (1.03 g, 2.0 mmol), 740 mg (yield: 71%) of the title compound was obtained in the same manner as in Example 1, using p-bromobenzyl bromide (550 mg, 2.2 mmol). A portion of the compound obtained was recrystallized from ethanol-ethyl acetate (1:1) to provide a sample for instrumental analysis.

Melting point: 212°–213° C. (decomposed)

Elementary analysis: for $C_{18}H_{18}N_2O_6Br_2$ Calculated: C, 41.72; H, 3.50; N, 5.41 Found: C, 41.71; H, 3.33; N, 5.42

Example 4

1-{(5-O-(3-chlorobenzyl)-$\beta$-D-arabinofuranosyl}-(E)-5-(2-bromovinyl)uracil (Compound 4)

From the starting compound 1 (1.03 g, 2 mmol), 670 mg (yield: 71%) of the title compound was obtained in the same manner as in Example 1, using m-chlorobenzyl bromide (452 mg, 2.2 mmol). A portion of the compound obtained was recrystallized from ethanol-ethyl acetate (1:1) to provide a sample for instrumental analysis.

Melting point: 194°–195° C. (decomposed)

Elementary analysis: for $C_{18}H_{18}N_2O_6BrCl$ Calculated: C, 45.64; H, 3.83; N, 5.91 Found: C, 45.63; H, 3.75; N, 6.04

Example 5

1-{5-O-(4-methylbenzyl)-$\beta$-D-arabinofuranosyl}(E)-5-(2-bromovinyl)uracil (Compound 5)

From the starting compound 1 (1.03 g, 2 mmol), 620 mg (yield: 68%) of the title compound was obtained in the same manner as in Example 1, using p-methylbenzyl chloride (407 mg, 2.2 mmol). A portion of the compound obtained was recrystallized from ethanol-ethyl acetate (1:1) to provide a sample for instrumental analysis.

Melting point: 216°–217° C. (decomposed)

Elementary analysis: for $C_{19}H_{21}N_2O_6Br$ Calculated: C, 50.35; H, 4.67; N, 6.18 Found: C, 50.28; H, 4.57; N, 6.16

Example 6

1-{(5-O-(4-fluorobenzyl)-β-D-arabinofuranosyl}-(E)-5-(2-bromovinyl)uracil (Compound 6)

From the starting compound 1 (1.03 g, 2 mmol), 527 mg (yield: 58%) of the title compound was obtained in the same manner as in Example 1, using p-fluorobenzyl chloride (416 mg, 2.2 mmol). A portion of the compound obtained was recrystallized from ethanol-ethyl acetate (1:1) to provide a sample for instrumental analysis.

Melting point: 212°–213° C. (decomposed)

Elementary analysis: for $C_{18}H_{18}N_2O_6BrF$ Calculated: C, 47.28; H, 3.97; N, 6.13 Found: C, 47.15; H, 4.08; N, 6.07

Example 7

1-{(5-O-(4-methoxybenzyl)-β-D-arabinofuransyl}-(E)-5-(2-bromovinyl)uracil (Compound 7)

From the starting compound 1 (1.03 g, 2 mmol), 178 mg (yield: 19%) of the title compound was obtained in the same manner as in Example 1, using p-methoxybenzyl chloride (345 mg, 2.2 mmol) and tetraethylammonium iodide (566 mg, 2.2 mmol). A portion of the compound obtained was recrystallized from ethanol to provide a sample for instrumental analysis.

Melting point: 183°–184° C. (decomposed)

Elementary analysis: for $C_{19}H_{21}N_2O_7Br$ Calculated: C, 48.63; H, 4.51; N, 5.97 Found: C, 48.58; H, 4.42; N, 5.72

Example 8

1-{5-O-(2-chlorobenzyl)-β-D-arabinofuranosyl}-(E)-5-(2-bromovinyl)uracil (Compound 8)

From the starting compound 1 (1.03 g, 2 mmol), 115 mg (yield: 12%) of the title compound was obtained in the same manner as in Example 1, using o-chlorobenzyl chloride (354 mg, 2.2 mmol) and tetraethylammonium iodide (566 mg, 2.2 mmol). A portion of the compound obtained was recrystallized from ethanol to provide a sample for instrumental analysis.

Melting point: 197°–198° C. (decomposed)

Elementary analysis: for $C_{18}H_{18}N_2O_6BrCl$ Calculated: C, 45.64; H, 3.83; N, 5.91 Found: C, 45.55; H, 3.52; N, 5.76

Example 9

1-{5-O-(3,4-dichlorobenzyl)-β-D-arabinofuranosyl}-(E)-5-(2-bromovinyl)uracil (Compound 9)

From the starting compound 1 (1.03 g, 2 mmol), 356 mg (yield: 35%) of the title compound was obtained in the same manner as in Example 1, using 3,4-dichlorobenzyl chloride (430 mg, 2.2 mmol) and tetraethylammonium iodide (566 mg, 2.2 mmol). A portion of the compound obtained was recrystallized from ethanol to provide a sample for instrumental analysis.

Melting point: 191°–192° C. (decomposed)

Elementary analysis: for $C_{18}H_{17}N_2O_6BrCl_2$ Calculated: C, 42.55; H, 3.37; N, 5.51 Found: C, 42.44; H, 3.27; N, 5.40

Example 10

1-{5-O-(2,4-dichlorobenzyl)-β-D-arabinofuranosyl}-(E)-5-(2-bromovinyl)uracil (Compound 10)

From the starting compound 1 (1.03 g, 2 mmol), 382 mg (yield: 38%) of the title compound was obtained in the same manner as in Example 1, using 2,4-dichlorobenzyl chloride (430 mg, 2.2 mmol) and tetraethylammonium iodide (566 mg, 2.2 mmol). A portion of the compound obtained was recrystallized from ethanol to provide a sample for instrumental analysis.

Melting point: 192°–193° C. (decomposed)

Elementary analysis: for $C_{18}H_{17}N_2O_6BrCl_2$ Calculated: C, 42.55; H, 3.37; N, 5.51 Found: C, 42.53; H, 3.18; N, 5.43

Example 11

1-{5-O-(4-isopropylbenzyl)-β-D-arabinofuranosyl}-(E)-5-(2-bromovinyl)uracil (Compound 11)

From the starting compound 1 (1.03 g, 2 mmol), 340 mg (yield: 35%) of the title compound was obtained in the same manner as in Example 1, using p-isopropylbenzyl chloride (371 mg, 2.2 mmol) and sodium iodide (330 mg, 2.2 mmol), with an additional isolation and purification step performed by silica gel column chromatography. A portion of the compound obtained was recrystallized from ethanol to provide a sample for instrumental analysis.

Melting point: 189°–190° C. (decomposed)

Elementary analysis: for $C_{21}H_{25}N_2O_6Br$ Calculated: C, 52.40; H, 5.24; N, 5.82 Found: C, 52.30; H, 5.36; N, 5.56

Example 12

1-{(5-O-(2-fluorobenzyl)-β-D-arabinofuranosyl}-(E)-5-(2-bromovinyl)uracil (Compound 12)

From the starting compound 1 (1.03 g, 2.0 mmol), 416 mg (yield: 46%) of the title compound was obtained in the same manner as in Example 1, using o-fluorobenzyl bromide (416 mg, 2.2 mmol). A portion of the compound obtained was recrystallized from ethanol to provide a sample for instrumental analysis.

Melting point: 197°–198° C. (decomposed)

Elementary analysis: for $C_{18}H_{18}N_2O_6BrF$ Calculated: C, 47.28; H, 3.97; N, 6.13 Found: C, 47.24; H, 4.02; N, 5.09

Example 13

1-(5-O-ethyl-β-D-arabinofuranosyl)-(E)-5-(2-bromovinyl)uracil (Compound 13)

From the starting compound 1 (1.03 g, 2.0 mmol), 110 mg (yield: 13%) of the title compound was obtained in the same manner as in Example 1, using ethyl iodide (334 mg, 2.2 mmol), with an additional isolation and purification step performed by silica gel column chromatography. A portion of the compound obtained was recrystallized from ethanol to provide a sample for instrumental analysis.

Melting point: 178°–179° C. (decomposed)

Elementary analysis: for $C_{13}H_{17}N_2O_6Br$ Calculated: C, 41.40; H, 4.54; N, 7.43 Found: C, 41.53; H, 4.46; N, 7.34

Example 14

1-{5-O-(2-chlorobenzyl)-β-D-arabinofuranosyl}-(E)-5-(2-chlorovinyl)uracil (Compound 14)

From the starting compound 2 (946 mg, 2.0 mmol), 343 mg (yield: 40%) of the title compound was obtained in the same manner as in Example 1, using o-chlorobenzyl bromide (354 mg, 2.2 mmol). A portion of the compound obtained was recrystallized from ethanol to provide a sample for instrumental analysis.

Elementary analysis: for $C_{18}H_{18}N_2O_6Cl_2$ Calculated: C, 50.37; H, 4.23; N, 6.53 Found: C. 50.24; H, 4.12; N, 6.49

Example 15

1-(5-O-n-propyl-$\beta$-D-arabinofuranosyl)-(E)-5-(2-bromovinyl)uracil (Compound 15)

From the starting compound 1 (517 mg, 1.0 mmol), 110 mg (yield: 28%) of the title compound was obtained in the same manner as in Example 1, using propyl iodide (187 mg, 1.2 mmol), with an additional isolation and purification step performed by silica gel column chromatography. A portion of the compound obtained was recrystallized from ethanol to provide a sample for instrumental analysis.

Melting point: 184°–185° C. (decomposed)

Elementary analysis: for $C_{14}H_{19}N_2O_6Br$ Calculated: C, 42.98; H, 4.90; N, 7.16 Found: C, 42.98; H, 4.84; N, 7.28

Example 16

1-{5-O-(2,4-dichlorobenzyl)-$\beta$-D-arabinofuranosyl}-(E)-5-(2-chlorovinyl)uracil (Compound 16)

From the starting compound 2 (472 mg, 1.0 mmol), 222 mg (yield: 48%) of the title compound was obtained in the same manner as in Example 1, using 2,4-dichlorobenzyl chloride (225 mg, 1.15 mmol) and sodium iodide (180 mg, 1.2 mmol). A portion of the compound obtained was recrystallized from ethanol to provide a sample for instrumental analysis.

Melting point: 201°–202° C. (decomposed)

Elementary analysis: for $C_{18}H_{17}N_2O_6Cl_3$ Calculated: C, 46.62; H, 3.70; N, 6.04 Found: C, 46.85; H, 3.56; N, 6.18

Example 17

1-(5-O-ethyl-$\beta$-D-arabinofuranosyl)-(E)-5-(2-chlorovinyl)uracil (Compound 17)

From the starting compound 2 (472 mg, 1.0 mmol), 123 mg (yield: 37%) of the title compound was obtained in the same manner as in Example 1, using ethyl iodide (187 mg, 1.2 mmol), with an additional isolation and purification step performed by silica gel co lumn chromatography. A portion of the compound obtained was recrystallized from ethanol to provide a sample for instrumental analysis.

Melting point: 208° C. (decomposed)

Elementary analysis: for $C_{13}H_{17}N_2O_6Cl$ Calculated: C, 46.93; H, 5.15; N, 8.42 Found: C, 46.97; H, 5.09; N, 8.36

Example 18

1-{5-O-(2,4-dichlorobenzyl)-$\beta$-D-arabinofuranosyl}-(E)-5-(2-iodovinyl)uracil (Compound 18)

From the starting compound 3 (451 mg, 0.8 mmol), 189 mg (yield: 43%) of the title compound was obtained in the same manner as in Example 1, using 2,4-dichlorobenzyl chloride (172 mg, 1.6 mmol) and sodium iodide (132 mg, 0.8 mmol). A portion of the compound obtained was recrystallized from ethanol to provide a sample for instrumental analysis.

Melting point: 197°–198° C. (decomposed)

Elementary analysis: for $C_{18}H_{17}N_2O_6Cl_2I$ Calculated: C, 38.94; H, 3.09; N, 5.05 Found: C, 39.11; H, 3.00; N, 5.14

Example 19

1-(5-O-ethyl-$\beta$-D-arabinofuranosyl)-(E)-5-(2-iodovinyl)uracil (Compound 19)

From the starting compound 3 (451 mg, 0.8 mmol), 91 mg (yield: 27%) of the title compound was obtained in the same manner as in Example 1, using ethyl iodide (137 mg, 0.88 mmol), with an additional isolation and purification step performed by silica gel column chromatography. A portion of the compound obtained was recrystallized from ethanol to provide a sample for instrumental analysis.

Melting point: 195°–196° C. (decomposed)

Elementary analysis: for $C_{13}H_{17}N_2O_6I$ Calculated: C, 36.81; H, 4.04; N, 6.60 Found: C, 37.06; H, 3.90; N, 6.71

Example 20

1-(3-O-2,4-dichlorobenzyl-$\beta$-D-arabinofuranosyl)-(E)-5-(2-bromovinyl)uracil (Compound 20)

The starting compound 4 (108 mg, 0.2 mmol) was dissolved in 4 ml of anhydrous tetrahydrofuran. To this solution was added 15.3 mg (2 equivalents) of 60% oily sodium hydride under ice-cooling, and the mixture was stirred for 30 minutes. To this mixture were then added 36 mg (1.2 equivalents) of sodium iodide and 0.047 g (1.2 equivalents) of 2,4-dichlorobenzyl chloride, and the mixture was stirred at room temperature for 15 hours. The reaction mixture was partitioned between ethyl acetate and aqueous ammonium chloride. The organic layer was washed with a saline solution and then concentrated to dryness over anhydrous sodium sulfate. The residue was subjected to silica gel column chromatography to isolate the product, which was dissolved in 4 ml of dioxane. To this solution was added 1 ml of 1 N hydrochloric acid, and the mixture was stirred at 50° C. for 1 hour. 50 ml of ethyl acetate was added to the reaction solution, and the mixture was washed with a saturated sodium hydrogencarbonate solution and a saturated saline solution and dehydrated over anhydrous sodium sulfate. The organic phase was then concentrated to dryness. The residue was chromatographed in a silica gel (7.5 g) column for isolation, and the product was recrystallized from a 9:1 solution of water and ethanol to obtain 60.3 mg (yield: 59%) of the title compound.

Melting point: 135°–136° C. (decomposed)

Elementary analysis: for $C_{18}H_{17}N_2O_6BrCl_2$ Calculated: C, 42.55; H, 3.37; N, 5.51 Found: C, 42.72; H, 3.38; N, 5.45

Example 21

1-(3-O-ethyl-$\beta$-D-arabinofuranosyl)-(E)-5-(2-bromovinyl)uracil (Compound 21)

The starting compound 4 (327 mg, 0.6 mmol) was dissolved in 12 ml of anhydrous tetrahydrofuran. To this solution was added 45.9 mg (2 equivalents) of 60% oily sodium hydride under ice-cooling, and the mixture was stirred for 30 minutes. To this mixture were then added 112 mg (1.2 equivalents) of iodoethane, and the mixture was stirred at room temperature for 15 hours. The reaction mixture was partitioned between ethyl acetate and aqueous ammonium chloride. The organic layer was washed with a saline solution and concentrated to dryness over anhydrous sodium sulfate. The residue was chromatographed a silica gel column to isolate the product, which was dissolved in 4 ml of dioxane. To this solution was added 1 ml of 1N hydrochloric acid, and the mixture was stirred at 50° C. for 1 hour. 50 ml of ethyl acetate was added to the reaction mixture, and the mixture was washed with a saturated sodium hydrogencarbonate solution and a saturated saline solution and dehydrated over anhydrous sodium sulfate. The organic layer was then concentrated to dryness. The residue was chromatographed in a silica gel (7.5 g) column for isolation, and the product was recrystallized from a 9:1 solution of water and ethanol to obtain 60.3 mg (yield: 27%) of the title compound.

Melting point: 170°–171° C. (decomposed)

Elementary analysis: for $C_{13}H_{17}N_2O_6Br$ Calculated: C, 41.40; H, 4.54; N, 7.43 Found: C, 41.59; H, 4.41; N, 7.38

Test Example 1

Method:

A test compound suspended in a saline containing 0.5% CMC was orally administered (100 μmol/kg) to ICR mice (6 weeks old, male). The blood was collected at 4, 8 and 12 hours after the administration, and the concentration of 1-$\beta$-D-arabinofuranosyl-(E)-5-(2-bromovinyl)uracil (BVAU) in the blood was measured by high-performance liquid chromatography (HPLC) (column used: Inertsil OSD-2 manufactured by Gaschro Kogyo K.K.).

Results:

The results are shown in Table 1.

TABLE 1

| Test Compound | Concentration of BVAU in Blood (μg/ml) | | |
|---|---|---|---|
| | after 4 hrs. | after 8 hrs. | after 12 hrs. |
| Compound 4 | 4.2 | 2.1 | 0.5 |
| Compound 6 | 5.1 | 3.2 | 1.3 |
| Compound 8 | 12.4 | 3.8 | 1.4 |
| Compound 9 | 7.1 | 3.4 | — |
| Compound 10 | 7.7 | 4.1 | 1.5 |
| Compound 12 | 9.4 | — | 1.4 |
| Compound 13 | 10.9 | 2.5 | 1.0 |
| Compound 21 | 7.2 | 3.6 | 0.9 |
| BVAU | 3.4 | 1.2 | 0.1 |

(Note)
In the table, "—" means that the measurement was not conducted.

Preparation Example 1

| Preparation of Tablet: | |
|---|---|
| Compound of the present invention | 10 g |
| Corn starch | 65 g |
| Carboxymethyl cellulose | 20 g |
| Polyvinylpyrrolidone | 3 g |
| Calcium stearate | 2 g |

| -continued | |
|---|---|
| Preparation of Tablet: | |
| Total | 100 g |

A tablet preparation weighing 100 mg/tablet is prepared by a conventional method.

Preparation Example 2

| Preparation of Powder and Capsule: | |
|---|---|
| Compound of the present invention | 20 g |
| Crystalline cellulose | 80 g |
| Total | 100 g |

Both of the above powders are mixed to prepare a powder preparation. Further, a hard capsule No. 5 is filled with 100 mg of the powder preparation to prepare a capsule preparation.

INDUSTRIAL APPLICABILITY

As is clear from the results of Test Example, the concentration of XVAU in blood is kept high for many hours when the compounds of the present invention are administered orally. For this reason, it can be expected that diseases caused by a virus belonging to herpesvirus are effectively cured with less amount of a medicine and/or fewer times of administration of the medicine.

We claim:

1. A 1-$\beta$-D-arabinofuranosyl-(E)-5-(2-halogenovinyl)uracil compound represented by the following formula (I):

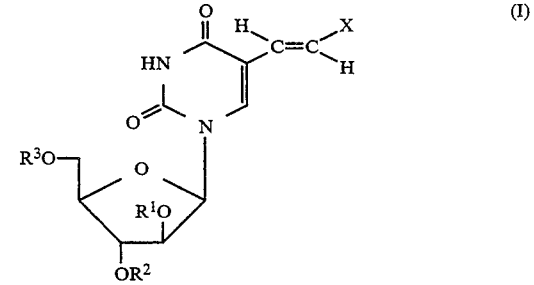

wherein X represents a halogen; and wherein $R^1$ and $R^2$ are hydrogen and $R^3$ is alkyl having 1 to 10 carbon atoms.

2. The compound as set forth in claim 1 wherein $R^3$ is selected from the group consisting of methyl, ethyl, n-propyl, i-propyl, n-butyl, i-butyl, sec-butyl, tert-butyl, n-pentyl, i-pentyl, neo-pentyl, n-hexyl, i-hexyl, n-heptyl, n-octyl, n-nonyl and n-decyl.

3. A pharmaceutical composition consisting essentially of, as an active ingredient, the compound of claim 1 with a pharmaceutically acceptable carrier, which is in the form of a preparation suitable for oral administration.

* * * * *